United States Patent [19]
Weeks

[11] Patent Number: 5,891,423
[45] Date of Patent: *Apr. 6, 1999

[54] METHODS OF CONTROLLING DUST AND COMPOSITIONS PRODUCED THEREBY

[75] Inventor: George Weeks, Danbury, Conn.

[73] Assignee: Clairol, Incorporated, New York, N.Y.

[ * ] Notice: The term of this patent shall not extend beyond the expiration date of Pat. No. 5,698,186.

[21] Appl. No.: 950,015

[22] Filed: Oct. 14, 1997

Related U.S. Application Data

[63] Continuation of Ser. No. 443,303, May 17, 1995, Pat. No. 5,698,186, which is a continuation of Ser. No. 161,356, Dec. 2, 1993, abandoned, which is a continuation of Ser. No. 930,645, Aug. 17, 1992, abandoned.

[51] Int. Cl.$^6$ .......................... A61K 7/07; A61K 7/135; B01J 2/30
[52] U.S. Cl. ................................ 424/62; 8/111; 252/88.1; 264/117; 424/489
[58] Field of Search ........................... 424/62, 489, 490; 252/88.1; 264/117; 8/101, 107, 110, 111

[56] References Cited

U.S. PATENT DOCUMENTS

| | | | |
|---|---|---|---|
| 3,726,967 | 4/1973 | Vorsatz et al. | 424/62 |
| 3,838,064 | 9/1974 | Vogt et al. | 252/384 |
| 3,838,092 | 9/1974 | Vogt et al. | 524/546 |
| 3,993,584 | 11/1976 | Owen et al. | 252/383 |
| 4,016,090 | 4/1977 | Nakagawa et al. | 252/186.38 |
| 4,116,365 | 9/1978 | Morganroth | 222/92 |
| 4,170,637 | 10/1979 | Pum | 424/62 |
| 4,247,537 | 1/1981 | Lunn et al. | 424/62 |
| 4,507,278 | 3/1985 | DeMarco et al. | 424/62 |
| 5,224,964 | 7/1993 | Shami | 8/405 |
| 5,294,436 | 3/1994 | Cope et al. | 424/62 |
| 5,480,457 | 1/1996 | Dickson et al. | 8/111 |
| 5,551,454 | 9/1996 | Goncalves | 132/208 |
| 5,612,022 | 3/1997 | Tricaud et al. | 424/62 |
| 5,622,691 | 4/1997 | Tricaud et al. | 424/62 |
| 5,674,476 | 10/1997 | Clausen et al. | 424/62 |
| 5,698,186 | 12/1997 | Weeks | 424/62 |
| 5,783,175 | 7/1998 | Schultz et al. | 424/62 |

OTHER PUBLICATIONS

Ullmann's Encyclopedia of Industrial Chemistry. 5th, Completely Revised Edition, vol. B2: Unit Operations I, Particle Technology: Size Enlargement. pp. 7–1 to 7–3. (1988).

*Primary Examiner*—Robert H. Harrison
*Attorney, Agent, or Firm*—Anthony M. Santini; Charles J. Zeller

[57] ABSTRACT

Method of treating dry, free flowing, dust forming compositions with selected liquids to agglomerate a portion of the particles into groups of particles of sufficient size so that the treated compositions are substantially dust free and retain their free flowing properties, and the compositions produced by such treatment.

22 Claims, No Drawings

METHODS OF CONTROLLING DUST AND COMPOSITIONS PRODUCED THEREBY

This application is a continuation of Application Ser. No. 08/443,303, filed May 17, 1995, U.S. Pat. No. 5,698,186, which is a continuation of Application Ser. No. 161,356, filed Dec. 2, 1993, abandoned, which is a continuation of Application Ser. No. 930,645, filed Aug. 17, 1992, abandoned.

FIELD OF THE INVENTION

This invention relates to methods of treating dry, free flowing, pulverulent, dust forming compositions to convert them to substantially dust free, pulverulent compositions without adversely affecting their dry, free flowing properties and to the compositions produced thereby. It relates especially to hair treatment compositions including powdered bleaches and hair dyes and their components.

BACKGROUND OF THE INVENTION

Dust, which is produced in large quantities as a result of handling, transporting and storage of particulate compositions, especially free flowing powders, is a constant source of annoyance and danger. It is irritating to the eyes and mucous membrane, especially the nasal passages. Constant exposure to dust may cause pulmonary disease either because of local tissue lacerations or because the dust particles serve as carriers for toxic microbes. Certain types of dust, particularly coal dust, form explosive mixtures when they attain critical concentrations.

Dust formation is a special annoyance in the field of hair treatment compositions such as those employed in hair dyeing and hair bleaching or frosting, or as a preliminary step to hair dyeing. Such compositions are well known. They normally contain powdered, oxidizing or bleaching compounds including peroxygenated salts such as perborates, percarbonates and persulfates. These include, for example, ammonium, alkali metal and alkaline earth metal peroxygenated salts. Often the particulate compositions will contain pH controlling agents such as silicates, phosphates and carbonates including, for example, sodium silicate. The presently preferred bleaching agents are persulfates and; of these, ammonium, potassium and sodium persulfate are most preferred. Often, the oxidizing powder will contain mixtures of persulfates such as ammonium, sodium and potassium persulfates. Other ingredients which may be utilized include thickeners, surfactants and the like. A swelling agent such as carboxymethyl cellulose or a vegetable gum is often added to give an emollient property to the final product.

For convenience, the hair treating compositions are provided as dry, free flowing powders which may contain a hydrogen peroxide precursor and are taken up in aqueous media just prior to use. If there is no precursor, the aqueous media will contain hydrogen peroxide. While such compositions are convenient, they do manifest a number of difficulties.

One such difficulty is dust formation caused by collision and abrasion of powder particles with each other during handling, storage and transportation. Another, is that, if the particles are not of uniform size, the finer particles, those most likely to produce dust, are at the top of the package.

Hair treatment compositions are usually provided as fine grained powders containing a number of discrete, dust forming particles of various ingredients with particle sizes below about 40 microns together with larger particles, even as high as 1000 microns. It is the particles of a size up to about 40 microns which are especially troublesome dust farmers. Often, there is a lack of uniformity in the compositions attributed, at least in part, to the fact that the various particles forming them have different apparent densities which causes them to separate during transportation and storage. As a result, the heavier particles concentrate at the bottom of the package while the lighter particles migrate to the top. This lack of uniformity causes variations in the hair treatment results which can be achieved because the portions withdrawn from the package for use are not of uniform composition. One way of alleviating the problem is by appropriate mixing, but this is inconvenient, time consuming and often overlooked. Another possibility is to prepare the compositions with particles of uniform small size, but dust forms every easily from fine particles.

There are many examples of adding various types of liquids or hydrophilic materials to powders to prevent dust formation. In extreme cases, sufficient amounts of such materials are added so that the powders are actually converted to pastes or creams. Generally speaking, these procedures have not been satisfactory because the additions tend to diminish the desirable free flowing characteristics of the powders and, in the case of creams and pastes, totally destroy these properties. Or, if insufficient additive is employed, the composition remains free flowing but still forms appreciable amounts of dust.

Hydrophilic materials, although recommended for producing dust free compositions, are not particularly recommended for hair treatment compositions because the components of such compositions react rapidly with water. Two problems arise with hair bleaches. These are:

1. Ammonium salts and alkali (generally, ammonium persulfate and sodium metasilicate) generate ammonia which is necessary for hair bleaching and will be lost by reacting with water. Further, sodium metasilicate after reacting with the ammonium salt will solidify, being converted to silica, and cannot be redissolved.

2. Persulfates decompose when moist or when heated excessively but the decomposition is more rapid when a moist persulfate is heated. Therefore, the bleaching ability is decreased if it remains wet. It is also decreased if an attempt is made to dry by heating.

For convenience, this invention will be described principally as it relates to hair bleaching compositions, although the terms "hair treating or treatment compositions" should be understood to include both dyes and bleaches. However, it is not limited to hair treating compositions. It may, for example, be employed with alkali metal and ammonium persulfates which are utilized not only in hair bleaching compositions but also in the paint and in the polymer industries.

Typical hair dying compositions which may be treated in accordance with this invention include oxidative, including auto-oxidative, dyes which may be provided as powdered primary intermediates and couplers. Many such products are known. Those which are presently employed on a wide scale include those listed in Table 1, below.

TABLE 1

| | |
|---|---|
| Primary Intermediates: | p-phenylenediamine |
| | p-aminophenol |
| | o-aminophenol |
| | N,N-bis(2-hydroxyethyl)p-phenylendiamine |
| | 2,5-diaminopyridine |
| | p-toluene diamine |

TABLE 1-continued

| Couplers: | resorcinol |
| --- | --- |
| | m-aminophenol |
| | 1-naphthol |
| | 5-amino-o-cresol |
| | 2-methylresorcinal |
| | 4,6-di(hydroxyethoxy)-meta-phenylenediamine |
| | meta-phenylenediamine |
| Auto-oxidative dyes | 2,4-diaminophenol |
| | benzene-1,2,4-triol |
| | toluene-2,4,5-triol |

Semipermanent dyes such as those listed in Table 2 are also included within the ambit of the invention.

TABLE 2

N-(2-Hydroxyethyl)-o-nitroaniline
4-Nitro-o-phenylenediamin
$N^1$-(2-Hydroxyethyl)-4-nitro-o-phenylenediamine
$N^1$-Tris(hydroxymethyl)methyl-4-nitro-o-phenylenadiamine
2-Amino-3-nitrophenol
2-Amino-4-nitrophenol
4-Amino-2-nitrophenol
2-Amino-5-nitrophenol
O,N-Bis(2-hydroxyethyl)-2-amino-5-nitrophenol
N-(2-Hydroxyethyl)-2-amino-5-nitroanisole
4-Amino-3-nitrophenol
N-(2-Hydroxyethyl)-4-amino-3-nitrophenol
N-(2-Hydroxyethyl)-4-amino-3-nitroanisole
1-(3-Methylamino-4-nitrophenoxy)propane-2,3-diol
3-Methylamino-4-nitrophenoxyethanol
2-Nitro-p-phenylenediamine
N1-(2-Hydroxyethyl)-2-nitro-p-phenylenediamine
N4-(2-Hydroxyethyl)-2-nitro-p-phenylenediamine
N1-Methyl-2-nitro-p-phenylenediamine
N1,N4,N4-Tris(2-hydroxyethyl)-2-nitro-p-phenylenediamine
N4-(2-Hydroxyethyl)-N1,N4-dimethyl-2-nitro-p-phenylenediamine
N4-(2,3-Dihydroxypropyl)-N,N4-dimethyl-2-nitro-p-phenylenediamine
4-Nitro-m-phenylenediamine
Picramic Acid
N-Methyl-iso-picramic acid
4-Amino-2-nitrodiphenylamine
4-Hydroxy-2'-nitrodiphenylamine
4-(p-Aminophenylazo)-N,N-bis(2-hydroxyethyl)aniline
1,4,5,8-Tetraminoanthraquinone
1,4-Diaminoanthraquinone
1-Amino-4-methylaminoanthraquinone
1-(2-Hydroxyethylamino)-4-methylaminoanthraquinone
2,4-Diamino-2'-hydroxy-5'-nitroazobenzene-5'-sulphonic acid (Sodium salt)

The various liquids and other materials which have heretofor been employed as dust inhibitors in hair bleaching powders have been specific in their usages and have not taken into account the aesthetics of the final product or the compatibility of the deducting agent with the bleach components, or with the hair.

According to German Published Application Number DE 40 26 235 A1, dust free compositions are provided by mixing ammonium, potassium and sodium persulfate granulates having a particle diameter of 0.1 to 0.6 cm with a water soluble thickener, a wetting agent and/or an emulsifier.

U.S. Pat. Nos. 3,838,064; 3,838,092; 3,947,089 and 3,993,584 all relate to the use of special grades of polytetrafluoroethylene (Teflon) to control dust generated by fine powders. This procedure is not completely satisfactory because it is expensive and requires special mixing equipment. Additionally, when used in hair bleaches the small pieces of Teflon become trapped or entangled in the hair similar to gum.

U.S. Pat. No. 3,726,967 describes the use of water soluble polyvinylpyrrolidone or glucose in homogeneous hair bleaching compositions. These additives are solids, require specialized equipment for coating the particles and are not described as reducing dust formation.

U.S. Pat. No. 4,170,637 and German Patent Number DE 3 814 356 C both describe the formation of hair bleaching paste compositions with an anhydrous organic carrier. Such compositions lack the convenience of free flowing powders, are much more difficult to manufacture and, because measurement is difficult, they must be packaged for individual use and are, therefore, not convenient or cost efficient for salon use.

BRIEF DESCRIPTION OF THE INVENTION

It has now been discovered that powders, particularly dry, free flowing hair treatment compositions and their components which are dust forming due to the presence of particles having a particle size less than about 40 microns can be rendered substantially dust free by treatment with an inert liquid to join the particles together into groups of agglomerated particles, the members of the thus formed groups having a particle size greater than about 40 microns.

More specifically, the effect of treating a dry, free flowing, dust forming composition using the methods of this invention is to convert it to a composition which is still free flowing but in which a number of the smaller particles are joined together to form agglomerated groups of particles. The compositions of the invention therefore comprise dry, free flowing powders containing discrete particles virtually all of which have a particle size above about 40 microns together with agglomerated groups of particles, the particle size of each group of particles being greater than about 40 microns. Such compositions retain their dry, free flowing characteristics, but are substantially dust free. They are substantially free of discrete or agglomerated particles having a particle size less than about 40 microns, i.e. they are substantially free of dust forming particles.

DETAILED DESCRIPTION OF THE INVENTION

The original dry, free flowing, pulverulent, dust forming compositions are converted to products of the invention by treatment with selected inert liquids so that the particles adsorb the liquid on their surface. Such adsortion treatment can be conducted, for example, by dissolving the adsorbate in a suitable solvent, suspending the particles to be treated in the solution and evaporating the solvent. Alternatively, the selected adsorbate, with or without solvent, can be sprayed under pressure onto the surface of the dust forming powder while the powder is stirred or otherwise agitated in a high speed power blender. Other equivalent procedures will be known to those skilled in the art.

The selected liquid should be inert with respect to the other components in the composition, i.e. it should not chemically react with any of them, nor should it adversely affect their physical characteristics. It should not, for example, absorb water since water will adversely affect the stability of the compositions. Normally, anhydrous liquids will be employed.

Inert adsorbates suitable for use in the invention include liquids such as organic liquids, oils and waxes. Typical liquids which may be employed in the dedusting operation include, for example: mineral oils (both, heavy and light); petrolatums; hydrocarbons with ether linkages such as anhydrous 2-methoxyethyl ether and butyl phenyl ether; hydrocarbons with a short polyethylene glycol chain such as octoxynol-1; tributyrin; silicone oils such as dimethylpolysiloxanes and phenylmethyl polysiloxanes; fluorosilicone fluids such as General Electric Silicone FF150-10M; perfluoropolymethylisopropyl ethers such as the Fomblin fluids by Montefluos; natural oils, typically described as animal, vegetable or herbal oils such as anhydrous lanolin, olive oil, sesame seed oil, jojoba oil, wheat germ oil and apricot kernel oil.

The adsorbates utilized herein are referred to as "liquids". In fact, most of the adsorbates are liquid at ambient temperature. However, some waxes are solid or semi-solid at room temperature. Such products can be adsorbed from solution as described above. Alternatively, they can be heated to a temperature at which they liquify, and the liquid sprayed into a suspension of the powder. This procedure is also described above. The term "treating or treatment" as used herein with reference to the adsorbate refers to any technique which may be employed to adsorb the liquid onto the surface of the particles.

Any of a wide variety of solvents may be employed to dissolve the liquids utilized to treat the powders of this invention to form agglomerated groups of particles. Since the solvent will be evaporated to deposit the liquid adsorbate on the surface of the particles, the selected solvent will be relatively volatile. Any of a wide variety of polar and non-polar solvents may be utilized, as will be apparent from the list of suitable liquids which appears above. These include hydrocarbons, halogenated hydrocarbons, ethers and similar solvents, both aliphatic and aromatic. Hexane, heptane, ethylene dichloride and diethyl ether may be mentioned by way of example.

The presently preferred inert liquids are mineral oils and natural oils such as lanolin because they are easily available, relatively unexpensive and provide excellent results. Silicone oils such as dimethicone are especially preferred because they provide excellent deducting results and also function as hair conditioning agents.

The liquid additive appears to perform two functions in rendering the powder compositions of this invention substantially dust free after it in adsorbed on the surface of the particles. One function is that it serves as an adhesive to form agglomerates from the small particles. The second function is that it serves as a lubricant so that the particles do not abrade during handling and produce dust. The result is that the particle size range above 40 microns in the final product remains essentially the same. These are the agglomerated groups of particles. The consequence of the combination of adhesive and lubricating function is that the compositions of the invention remain free flowing and are dry in appearance.

As used in this specification and appended claims, the term percent by weight when referring to a particular component of a composition means the percent weight of that component based on the total weight of the composition.

As would be expected, the optimum effective amount of liquid for each dust forming particle base will vary with the selected liquid, the selected base and the method of treatment. However, an effective amount for a particular combination will be as defined above and easily determinable by use of any of the standard procedures normally employed to measure dust formation. Several are known in the art. These include, for example, air current methods, rotating drum methods and gravity methods.

Accordingly, the hair bleaching compositions of this invention comprise dry, free flowing particulate compositions containing hair bleaching components in the form of discrete particles and agglomerated particles having adsorbed thereon an effective amount of an inert liquid to adhere discrete particles to each other to form agglomerated particles having particle sizes greater than about 40 microns, with the result that the composition is substantially free of either discrete particles or agglomerated particles of a particle size less than about 40 microns. Typically, the amount of adsorbed inert liquid will be from about 10% to about 25% by weight, although appreciable variation from this range can be tolerated without adverse effect. The presently preferred range for most particle/liquid combinations is from about 14% to about 20% by weight.

While the invention has been described principally with reference to treatment of finished hair bleaching compositions to render them substantially dust free, it will be apparent that the separate components of the compositions may be individually treated and then mixed to form a final, substantially dust free composition of the invention. Thus, for example, persulfate salts such as ammonium, sodium and potassium persulfate which are the most irritating of the components may be treated by the process of the invention by the manufacturer prior to shipment to the actual blender. This, in fact, is a preferred embodiment of the invention since, as indicated above, ammonium, sodium and potassium persulfates are employed not only in the production of hair bleaching compositions, but also by paint and plastic manufacturers.

The following Table 3 illustrates the results which may be achieved by utilizing the process of this invention. In Table 3, Formulations A through C are hair bleaching compositions containing a mixture of ammonium persulfate and an alkali metal metasilicate together with conventional additives such as chelating agents and thickeners. Formulation A was dedusted by spray treatment with mineral oil so that the particles adsorbed about 17% by weight mineral oil. The particles of Formulation B adsorbed 25% silicone oil. In Formulation C, mineral oil was again utilized and the amount adsorbed was 10%. Formulation A is a test formulation. Formulations B and C are commercially available hair bleaching compositions. The last columns, identified as D and Dedusted D record the results with untreated potassium persulfate and the same product dedusted by adsorption of 10% petrolatum.

It will be seen from the Table 3 that the effect of treatment in accordance with this invention is to increase the percent by weight of larger particles and decrease the percent by weight of dust forming particles with particle sizes less than about 40 microns.

TABLE 3

Sieve Analysis of Bleaching Powders % by Weight

| Mesh Size (Retained by) | Particle Size Microns | Formulation A | Dedusted Formulation A | Formulation B | Dedusted Formulation B |
|---|---|---|---|---|---|
| 40 | >420 | 1.0 | 7.4 | 0.2 | 95.4 |
| 50 | >297 | 0.7 | 2.3 | 1.2 | 1.22 |
| 100 | >149 | 21.5 | 73.2 | 35.1 | 4.3 |
| 200 | >74 | 48.8 | 13.6 | 27.1 | 0.0 |
| 325 | >44 | 16.4 | 3.4 | 31.9 | 0.0 |
| 400 | >37 | 5.8 | 0.0 | 3.7 | 0.0 |
| thru 400 | <37 | 5.5 | 0.0 | 1.2 | 0.0 |

| Mesh Size (Retained by) | Particle Size Microns | Formulation C | Dedusted Formulation C | Formulation D | Dedusted Formulation D |
|---|---|---|---|---|---|
| 40 | >420 | 6.6 | 16.5 | 0.1 | 77.6 |
| 50 | >297 | 12.0 | 10.0 | 0.0 | 5.3 |
| 100 | >149 | 31.9 | 64.7 | 8.98 | 17.6 |

TABLE 3-continued

| Sieve Analysis of Bleaching Powders % by Weight | | | | | |
|---|---|---|---|---|---|
| 200 | >74 | 30.4 | 6.6 | 56.8 | 0.1 |
| 325 | >44 | 18.2 | 2.7 | 13.34 | 0.1 |
| 400 | >37 | 1.4 | 0.0 | 12.75 | 0.0 |
| thru 400 | <37 | 0.0 | 0.0 | 7.7 | 0.0 |

The process was found to be effective with a number of commercially available inert liquids and bleaching compositions. For example, (1) General Electric fluorosilicone fluid FF150-M was particularly effective at 20% and 25% with Matrix's So White Lite. Some dust was present at 15%. Lumping begun at 30%.

(2) 10% Witco Sonogel #9 yielded a dedusted product with Frosty Roulite which already contains 5% lanolin.

(3) 20% Witco Britol oil (a heavy mineral oil), 15% Witco Mineral Jelly #17 and 16% 2-methoxyethyl ether each produced dedusted L'Oreal's Quick Blue Powder.

(4) 15% Dow Corning 2000 fluid (1000 cs viscosity), a dimethylsiloxane, yields a suitable dedusted product with L'Oreal's Pure Platine.

(5) A mixture of 5% each of Super Corona Lanolin (anhydrous USP), FF150-10M and 2-methoxymethyl ether produced a dedusted product with L'Oreal's Pure Platine.

The following example is given by way of illustration only and should not be considered limitations of this invention, many variations of which are possible without departing from the spirit or scope thereof.

EXAMPLE 1

4.0 g of lanolin oil is dissolved in 40 mls of reagent grade hexane. 16 g of a hair bleaching composition containing a powdered mixture of ammonium, sodium and potassium persulfates, the particle size of all of the particles in the composition being from about 35 to 400 microns, is placed in a 250 ml round bottom flask and the lanolin oil/hexane solution is added with swirling. The round bottom flask is placed on a rotary evaporator and all of the hexane is removed under vacuum. If necessary, the walls of the round bottom flask are scraped with a spatula to remove all of the mixture. To assess the dustiness of a sample, 20 g are placed in a wide mouth 4 oz jar and the lid is secured. The jar is shaken and the lid is immediately removed. Without any adsorbed lanolin oil, dust rises from the top of the jar for several minutes. With about 20% by weight adsorbed lanolin oil, no dust is seen.

What is claimed is:

1. A method of de-dusting a stable, dry, free-flowing, dust-forming peroxygenated salt-containing powder comprised of fine, discrete, pulverulent particles, wherein said method consists essentially of treating said dust-forming powder with a de-dusting amount of a substantially anhydrous inert liquid, wherein said liquid agglomerates dust-forming particles, yet maintains a stable, dry, free-flowing powder which is substantially free of dust.

2. The method of claim 1 wherein said agglomerated particles are in groups greater than about 40 microns in size.

3. The method of claim 1 wherein the dust-forming powder is treated with from about 10% to about 25% by weight of the inert liquid.

4. The method of claim 1 wherein said inert liquid is an oil.

5. The method of claim 4 wherein said oil is selected from the group consisting of mineral oil, silicone oil, natural oil, perfluoropolymethylisopropyl ether, tributyrin and mixtures thereof.

6. The method of claim 5 wherein said oil is mineral oil or natural oil.

7. The method of claim 6 wherein said oil is mineral oil.

8. The method of claim 1 wherein said powder comprises ammonium, alkali metal or alkaline earth metal peroxygenated salts or mixtures thereof.

9. The method of claim 8 wherein said powder is a hair bleaching or hair dyeing composition.

10. The method of claim 9 wherein the peroxygenated salts are persulfates.

11. The method of claim 10 wherein the persulfate is ammonium persulfate, sodium persulfate, potassium persulfate or a mixture thereof.

12. A stable, dry, free-flowing peroxygenated salt-containing powder which is substantially free of dust-forming particles wherein said particles have been agglomerated by a de-dusting amount of a substantially anhydrous inert liquid adsorbed on said particles.

13. The powder of claim 12 wherein said agglomerated particles are in groups greater than about 40 microns in size.

14. The powder of claim 12 wherein the amount of adsorbed inert liquid is from about 10% to about 25% by weight.

15. The powder of claim 12 wherein said inert liquid is an oil.

16. The powder of claim 15 wherein said oil is selected from the group consisting of mineral oil, silicone oil, natural oil, perfluoropolymethylisopropyl ether, tributyrin and mixtures thereof.

17. The powder of claim 16 wherein said oil is mineral or natural oil.

18. The powder of claim 16 wherein said oil is mineral oil.

19. The powder of claim 12 comprising ammonium, alkali metal, or alkaline earth metal peroxygenated salts or a mixture thereof.

20. The powder of claim 18 comprising a hair bleaching or hair dyeing composition.

21. The powder of claim 20 wherein the peroxygenated salts are persulfates.

22. The powder of claim 21 wherein the persulfate is ammonium persulfate, sodium persulfate, potassium persulfate or a mixture thereof.

* * * * *